United States Patent
Selva et al.

(10) Patent No.: US 9,125,823 B2
(45) Date of Patent: *Sep. 8, 2015

(54) CONTROLLED RELEASE PHARMACEUTICAL OR FOOD FORMULATION AND PROCESS FOR ITS PREPARATION

(75) Inventors: Stefano Selva, Bologna (IT); Leonardo Marchitto, Porto Recanati (TW); Giovanni Battista Ciottoli, Rome (IT); Lorella Ragni, Chiaravalle (IT); Vincenzo Russo, Rome (IT); Elisa Liberati, Rome (IT)

(73) Assignee: AZIENDE CHIMICHE RIUNITE ANGELINI FRANCESCO A.C.R.A.F. S.p.A., Rome (IT)

(*) Notice: Subject to any disclaimer, the term of this patent is extended or adjusted under 35 U.S.C. 154(b) by 144 days.

This patent is subject to a terminal disclaimer.

(21) Appl. No.: 13/139,192

(22) PCT Filed: Jan. 8, 2010

(86) PCT No.: PCT/EP2010/050137
§ 371 (c)(1),
(2), (4) Date: Jun. 10, 2011

(87) PCT Pub. No.: WO2010/084038
PCT Pub. Date: Jul. 29, 2010

(65) Prior Publication Data
US 2011/0318321 A1    Dec. 29, 2011

(30) Foreign Application Priority Data
Jan. 23, 2009  (EP) .................................. 09425014

(51) Int. Cl.
*A61K 9/20* (2006.01)
(52) U.S. Cl.
CPC ............... *A61K 9/205* (2013.01); *A61K 9/2054* (2013.01)
(58) Field of Classification Search
CPC ........................ A61K 9/2054; C08B 37/0009
USPC ........................................................ 424/452
See application file for complete search history.

(56) References Cited

U.S. PATENT DOCUMENTS

| | | | |
|---|---|---|---|
| 3,493,652 A * | 2/1970 | Hartman | 424/94.6 |
| 4,983,398 A * | 1/1991 | Gaylord et al. | 424/465 |
| 5,456,921 A | 10/1995 | Mateescu et al. | |
| 5,597,913 A | 1/1997 | Nicoletti et al. | |
| 6,440,949 B1 | 8/2002 | Zeng | |
| 6,607,748 B1 | 8/2003 | Lenaerts et al. | |
| 6,632,796 B1 | 10/2003 | Zeng | |
| 2006/0127387 A1 | 6/2006 | Zikria et al. | |
| 2006/0264357 A1 | 11/2006 | Zikria et al. | |
| 2008/0161234 A1 | 7/2008 | Andersch et al. | |
| 2009/0074867 A1 | 3/2009 | Marchitto et al. | |

FOREIGN PATENT DOCUMENTS

| | | |
|---|---|---|
| EP | 0 662 322 | 7/1995 |
| EP | 0 654 048 | 1/1997 |
| EP | 1 072 268 | 1/2001 |
| JP | 62 178505 | 8/1987 |
| JP | 63 290809 | 11/1988 |
| WO | 98 35992 | 8/1998 |
| WO | 99 47120 | 9/1999 |
| WO | 00 59477 | 10/2000 |
| WO | 2006 001766 | 1/2006 |
| WO | 2006 061142 | 6/2006 |
| WO | 2009 083561 | 7/2009 |

OTHER PUBLICATIONS

Snell, F. D. et al., "Colorimetric Methods of Analysis", D. Van Nostrand Company, Inc., New York, Edition $3_{rd}$, vol. 3, p. 204, (1954).
International Search Report Issued Feb. 17, 2010 in PCT/EP10/050137 filed Jan. 8, 2010.

* cited by examiner

*Primary Examiner* — Dennis J Parad
(74) *Attorney, Agent, or Firm* — Oblon, McClelland, Maier & Neustadt, L.L.P.

(57) ABSTRACT

The present invention relates to a controlled release pharmaceutical or food formulation comprising at least one active pharmaceutical or food ingredient dispersed in a mixture of a glycogen with a polysaccharide, and the process for its preparation. The invention also relates to a slow release system represented by a mixture of a glycogen with a polysaccharide, and its use for the preparation of slow release pharmaceutical or food formulations.

34 Claims, 7 Drawing Sheets

CONTROLLED RELEASE PHARMACEUTICAL OR FOOD FORMULATION AND PROCESS FOR ITS PREPARATION

FIELD OF THE INVENTION

This invention relates to a controlled release pharmaceutical or food formulation, and the process for its preparation.

In particular, the invention relates to a controlled release pharmaceutical or food formulation comprising at least one pharmaceutical or food active ingredient dispersed in a mixture of a glycogen with a polysaccharide, and the process for its preparation.

More particularly, the invention also relates to a controlled release system represented by a mixture of a glycogen with a polysaccharide.

STATE OF THE ART

Pharmaceutical forms or formulations for the administration of drugs contain auxiliary substances known as excipients in addition to the active pharmaceutical ingredient. These excipients are similarly included in food supplements which constitute a food formulation comprising a functional substance (vitamin, energy providing substance, protein, and so on), referred to below as a food active ingredient. In this description the term active ingredient if not otherwise specified, will be used to mean a pharmaceutical and/or food active ingredient without distinction. Similarly the term form or formulation, if not further specified, will be used to mean a pharmaceutical and/or food form or formulation without distinction.

Excipients have various important roles in the process of the manufacture, preservation and use of pharmaceutical or food formulations.

Depending upon their role, excipients are classified into filler excipients, production excipients, preservative excipients, presentation excipients and release excipients.

Excipients having a role as a filler comprise diluents used to increase the volume of formulations, absorbents used to absorb and retain moisture, and adsorbents used to adsorb gases, toxins and bacteria.

Excipients having a production role are lubricants used in the preparation of tablets which prevent powders from adhering to the dies or punches of tabletting machines, binders which impart compactness to formulations, glidants which improve the flow of powders, plasticisers and viscosity modifiers.

Excipients having a preservative role are useful for ensuring that formulations are stable in terms of chemical, physical, microbiological, toxicological and therapeutic characteristics. These excipients include antibiotics to prevent the growth of microorganisms, antioxidants to reduce the oxidative degradation of active ingredients, and chelating agents to complex metals which are capable of catalysing reactions that degrade active ingredients.

Excipients having a presentation role are used to make formulations more attractive to users and include flavourings, sweeteners and colouring agents.

Among the excipients which have a role in the release of active ingredients we distinguish disaggregating agents, which following contact with biological fluids encourage disaggregation of formulations, and polymers used as coating substances or matrices to obtain the time-modulated release of active ingredients.

Chemically modified polysaccharides of plant origin such as for example starch and its components (amylose and amylopectin) have been extremely successful in recent years because of their non-toxic and biodegradable properties.

U.S. Pat. No. 5,456,921 describes a slow-release pharmaceutical form comprising a mixture of active ingredient and a cross-linked polymer obtained from amylose cross-linked with epichlorohydrin or 2,3-dibromopropanol.

Patent application WO98/35992 describes a process for the preparation of a slow-release excipient based on starch with a high amylose content, comprising a gelatinisation step, a cross-linking step, a desalination step, a heat treatment step, and finally a step of drying the slow-release excipient.

U.S. Pat. No. 6,607,748 describes a process similar to the above in which the cross-linking step is performed before the gelatinisation step, and describes how smaller quantities of reagent are used in this way and a material with improved slow release properties is obtained.

Other examples of excipients used in the preparation of slow release oral formulations comprise celluloses, such as for example microcrystalline cellulose, alkylcellulose, hydroxyalkylcellulose, hydroxyalkylmethylcellulose, carboxyalkylcellulose, and other hydrophilic polysaccharides such as xanthan gum, various grades of carrageenans, and so on.

EP 662,322 describes a controlled release formulation comprising an active ingredient having a solubility of not more than 80 mg/ml, a hydroxypropylmethylcellulose derivative, and an agent capable of modifying erosion, such as lactose and polyoxylalkylene derivatives of propylene glycol, in addition to other inert materials such as binders and lubricants.

WO00/59477 describes a controlled release formulation which comprises one or more active ingredients, pregelatinised starch, and one or more hydrophilic polymers mainly selected from derivatives of cellulose, and preferably represented by hydroxypropylmethylcellulose and hydropropylcellulose.

WO2009/083561 describes a controlled-release pharmaceutical formulation comprising at least one active ingredient dispersed in a matrix comprising at least one glycogen and at least one alginate with alkaline-earth metal salts. The invention also relates to a slow-release excipient, to the process for its preparation and its use for the preparation of a slow-release pharmaceutical formulations. This application describes the formation of a hydrogel by using a specific manufacturing process employing salts of alginates with alkaline-earth metal salts.

WO2006/061142 describes a process for preparing an orally dispersible solid pharmaceutical form, comprising the step of coating the active ingredient with at least one hydrophilic carboxylate polymer, granulating the active ingredient thus obtained with a lipid compound and mixing the granulate thus obtained with at least one hydrophilic natural polymer. Therefore, this application does not relate to a controlled release formulation which releases the active ingredient over an extended period of time, typically over at least 6 hours, with a kinetics substantially of zero order, but to an orally dispersible formulation, with good palatability, that releases the drug in mouth in a period of time in less than 1.5 minutes.

Glycogen is a polysaccharide of predominantly animal origin mainly comprising molecules of D-glucose linked through glucoside α-1-4 bonds, with branches formed by glucoside α-1-6 bonds every five to ten glucose units. The number of branches and the degree of branching in glycogen vary according to the animal species from which it is obtained. The molecular weight of natural glycogen is of the order of $10^6$-$10^7$ Dalton. In nature glycogen is always bound to a protein, glycogenin, an enzyme associated with the process of cell glycogen synthesis.

The quality of a commercial glycogen depends on whether residual proteins (measured in terms of the quantity of nitrogen, expressed as ppm) and reducing sugars are present in greater or lesser quantity. EP 654,048 describes a high quality glycogen derivative with a reduced content of nitrogen and reducing sugars.

Glycogen is used as an emollient (as described in JP-A-87-178 505) and a hydrating agent (as described in JP-A-88-290 809) in the cosmetics sector, as an additive in the food sector, and as a humectant and lubricant in ophthalmic solutions (as described in WO99/47120).

SUMMARY OF THE INVENTION

The Applicant has noted that the slow release formulations known in the art have many disadvantages.

A first disadvantage lies in the fact that the release profile often varies from the ideal profile of zero kinetics (that is release at a constant rate), being observed that there is initially a very high release rate which then decreases, or an initially very low release rate which then increases, or again a rate which varies unpredictably.

A second disadvantage lies in the fact that in order to obtain suitable hardness and friability characteristics in industrial production formulations often require the addition of further excipients which further unforeseeably alter release kinetics.

A third disadvantage lies in the fact that the active ingredient is not completely released and absorbed, in that the pharmaceutical or food form often retains even up to more than 20% w/w of the active ingredient present therein, thus bringing about a loss in the effectiveness of the pharmaceutical or food form and an increase in costs.

Surprisingly, the Applicant has found that the mixture of a glycogen with a polysaccharide, preferably a cellulose or gum, in the presence of an active ingredient, makes it possible to obtain controlled release pharmaceutical or food formulations which overcome the disadvantages described above.

Accordingly, the present invention relates to a controlled release pharmaceutical or food formulation comprising at least one active ingredient dispersed in a mixture of a glycogen with a polysaccharide.

The term "controlled release pharmaceutical or food formulation" means a solid formulation for oral administration that achieves slow release of an active ingredient in the gastrointestinal tract over an extended period of time, typically over at least 1 hour, preferably over at least 3 hours, and more preferably over at least 6 hours.

The Applicant has found that the pharmaceutical or food formulation according to this invention is capable of releasing the active ingredient with release kinetics which are substantially of zero order, that is to say which are constant over time and independent of concentration.

Moreover, the Applicant has also observed that the pharmaceutical formulation according to the present invention shows hardness and friability characteristics which are suitable for industrial production without requiring addition of the excipients conventionally used for this purpose, such as for example diluents, binders and/or plasticisers.

The Applicant has also observed that, during the administration period under consideration, the pharmaceutical formulation according to this invention is able to release the active ingredient present therein almost completely, that is to say almost 100% w/w.

Finally, the Applicant has observed that release of the active ingredient takes place during a period of time up to twelve, twenty-four or more hours, thus permitting single daily administration.

Preferably, the formulation of the present invention maintains active ingredient level in the blood or target tissue within the therapeutic range for 2 hours or more, more preferably for 4 hours or more, and most preferably for 8 hours or more.

In another aspect, the present invention also relates to an excipient for the preparation of controlled release pharmaceutical or food formulations comprising a mixture of a glycogen with a polysaccharide.

In a further aspect, the present invention relates to a process for the production of a pharmaceutical or food form comprising at least one active ingredient dispersed in a mixture of glycogen with a polysaccharide which comprises the steps of:
  mixing said glycogen and said polysaccharide with said active ingredient, and
  manufacturing the desired pharmaceutical or food form.

Preferably, said process for the production of a pharmaceutical or food form comprises the step of:
  (i) mixing said glycogen and said polysaccharide with said active ingredient,
  (ii) granulating the composition obtained in step (i) and drying the resultant granulate,
  (iii) mixing the granulate obtained in step (ii) with a glidant agent,
  (iv) mixing the composition obtained in step (iii) with a lubricating agent, and
  (v) manufacturing the desired pharmaceutical or food form.

Advantageously said process for the production of a pharmaceutical or food form comprises the steps of:
  (a) mixing said glycogen with a glidant agent,
  (b) mixing the composition from step (a) with said active ingredient and said polysaccharide,
  (c) mixing the composition from step (b) with a lubricating agent, and
  (d) manufacturing the desired pharmaceutical or food form.

The Applicant has observed that the process of production according to the present invention is economically convenient, is readily suited to industrial application, offers high reproducibility and makes it possible to manufacture pharmaceutical forms such as for example tablets, or food forms such as for example supplements, with an improved release profile.

DETAILED DESCRIPTION OF THE INVENTION

Figure 1:
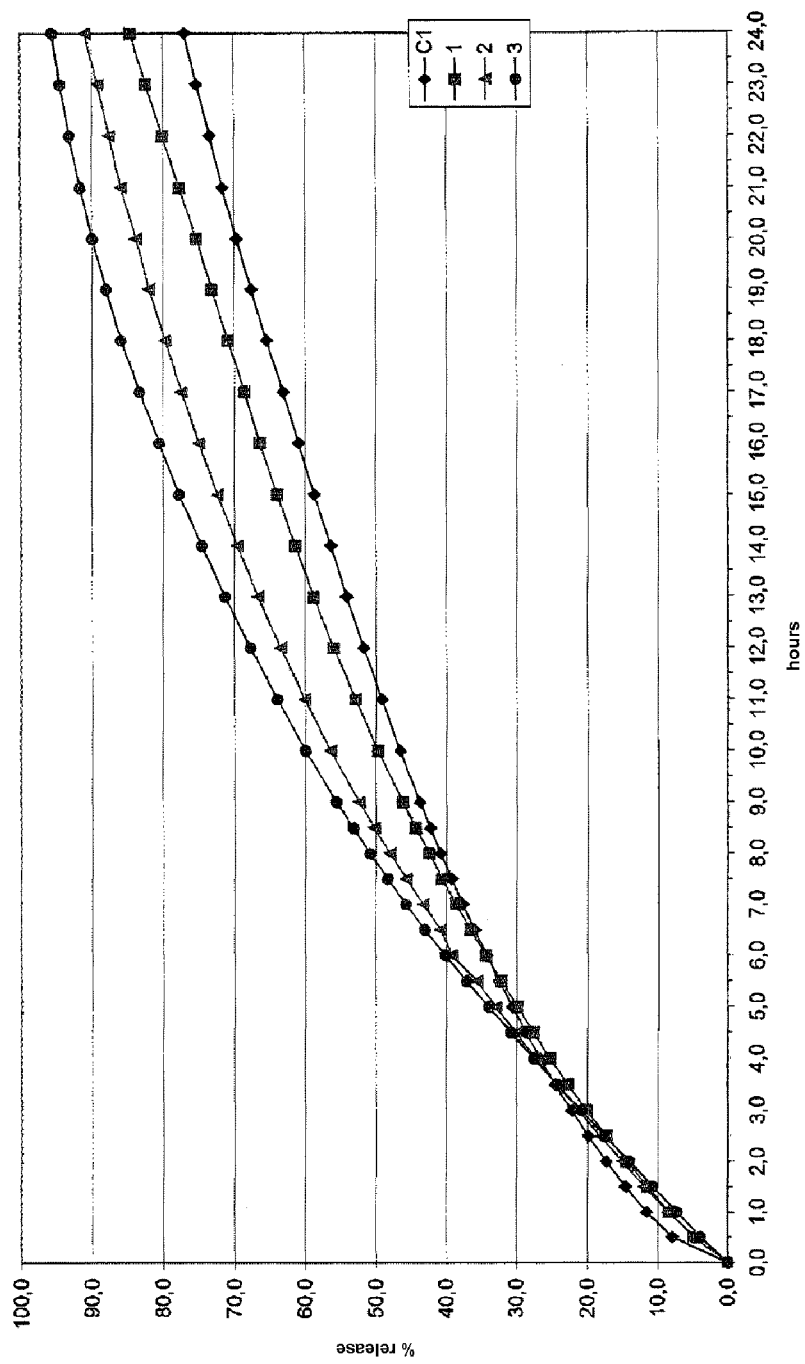
FIG. 1 illustrates the release profile for tablets 1, 2 and 3 in Example 1 compared with that for tablet C1.

In particular the present invention relates to a controlled release pharmaceutical or food formulation comprising at least one active ingredient dispersed in a mixture of glycogen with a polysaccharide.

The glycogen used in the present invention is obtained from natural glycogen which can be extracted from animals or fungi. Molluscs, in particular mussels (*Mytilus edulis* and *Mytilus gallus provincialis*) are a particularly useful source of glycogen because they are available in large quantities at low cost and contain a certain amount of glycogen (on average between 2.5% and 3.9% by weight). Other natural sources of glycogen include other bivalve molluscs such as clams, oysters, some species of gastropods or sea snails, as well as limpets (*Crepidula formicate*, the slipper limpet), as well as the organs of vertebrate animals which are rich in glycogen such as the liver and muscles.

The glycogen used in the present invention may be used as such as obtained from extraction processes or may be treated in subsequent purification procedures. As already mentioned previously, the quality of a commercial glycogen derives from the presence of larger or smaller quantities of protein residues (measured in terms of the quantity of nitrogen expressed as ppm) and reducing sugars.

For the purposes of the present invention it is preferred to use a glycogen having low reducing sugars and nitrogen content. Examples of commercial products which are preferably used in the present invention are glycogen produced and distributed by Sigma-Aldrich.

Preferably the glycogen used in the present invention comprises less than 1% by weight, more preferably less than 0.25% by weight of reducing sugars, measured using the method of F. D. Snell and Snell, "Colorimetric Methods of Analysis", New York, 1954, vol. III, p. 204).

Preferably the glycogen used in the present invention comprises less than 3,000 ppm of nitrogen, more preferably less than 1,000, and even more preferably less than 100 ppm of nitrogen, measured using the Kjeldahl method.

Preferably the glycogen used in the present invention is the glycogen Polglumyt™, the trade name of a deproteinated glycogen produced and distributed by A.C.R.A.F. S.p.A., Rome, Italy and obtained using the purification procedure described in patent EP 654048B1.

The polysaccharide used in the present invention is represented by celluloses, such as for example microcrystalline cellulose; alkylcelluloses such as methylcellulose, ethylcellulose and propylcellulose; hydroxyalkylcelluloses, such as hydroxymethylcellulose, hydroxyethylcellulose, hydroxypropylcellulose, hydroxybutylcellulose and hydroxypentylcellulose; hydroxyalkymethylcelluloses, such as hydroxyethylmethylcellulose, hydroxypropylmethylcellulose, hydroxyisopropylmethylcellulose, hydroxybutylmethylcellulose and hydroxyphenylmethylcellulose; hydroxyalkylalkylcelluloses such as hydroxypropylethylcellulose, hydroxypropylbutylcellulose and hydroxypropylpentylcellulose; carboxyalkylcelluloses such as carboxymethylcellulose, carboxyethylcellulose and carboxypropylcellulose; gums such as xanthan gum, gum arabic, gum tragacanth, gellan gum, ghatti gum; carrageenans, such as Kappa-carrageenan, Lambda-carrageenan, and Iota-carrageenan; mannanes, such as carob gum, tara gum, guar gum; and other hydrophilic polysaccharides such as agar, pectin, inulin, chitosan and chitin.

Preferably the polysaccharide used in the present invention is selected form the group comprising celluloses such as hydroxymethylcellulose, hydroxyethylcellulose, hydroxypropylcellulose, hydroxybutylcellulose, hydroxypentylcellulose, and hydroxypropylmethylcellulose; and gums such as xanthan gum, gum arabic, gum tragacanth, gellan gum, ghatti gum.

Advantageously, the polysaccharide used in the present invention is selected from the group comprising hydroxymethylcellulose, hydroxyethylcellulose, hydroxypropylmethylcellulose and xanthan gum.

Preferably the polysaccharide used in the present invention comprises a cellulose, more preferably hydroxypropylmethylcellulose, having a viscosity of between 100 and 100,000 mPa·s, preferably between 10,000 and 100,000 mPa·s, with reference to a 2% w/v aqueous solution at 20° C.

In preparation of the formulation according to the present invention the ratio by weight between glycogen and the polysaccharide preferably lies between 10:1 and 1:5, more preferably between 5:1 and 1:2, and even more preferably between 3:1 and 1:1.

The pharmaceutical or food active ingredient used in the present invention is selected from the group of active ingredients which can be administered orally. The present invention is particularly useful for active ingredients which require controlled administration over a period of time of more than twelve hours, preferably equal to or greater than twenty-four hours.

Useful examples of pharmaceutical active ingredients are selected from the group comprising analgesics, antipyretics, antibiotics, antihistamines, anxiolytics, anti-inflammatories, antacids, vasodilators, vasoconstrictors, stimulants, decongestants, anticoagulants, antiarrhythmics, hypoglycaemising agents, diuretics, antidepressants, antiasthmatics, antiemetics, antihypertensives and spasmolytics, anti-tumour agents, hormones, muscle relaxants, antiseptics, antimycotics, immunostimulants, immunomodulants, anti-migraine agents, anti-Parkinson agents, peptides, drugs of biological origin and biosimilar drugs.

The expression "drug of biological origin" means active ingredients obtained from plants or other biological sources and synthetic derivatives thereof.

The expression "biosimilar drug" means a new biological drug claimed to be similar to a reference medicinal product, which has been granted a marketing authorization.

Useful examples of food active ingredients are selected from the group comprising vitamins, minerals and plant extracts, mixtures of straight and branched amino acids, and biotechnology products.

The term "biotechnology products" means products obtained by biotechnology techniques, such as, for example, recombinant DNA technique, PCR (Polymerase Chain Reaction) technique, and the like.

Specific examples of pharmaceutical active ingredients preferably used in the present invention are ibuprofen, paracetamol, prulifloxacin, levocetirizine dihydrochloride, lorazepam, naproxene, ranitidine hydrochloride, isosorbide, nafazoline nitrate, piracetam, ticlopidine hydrochloride, propafenone hydrochloride, glimepiride, furosemide, verapamil, trazodone hydrochloride, flunisolide, dimenidrinate, diclofenac and its salts, ciprofloxacin, omeprazole, flurbiprofen, bindarit, sumatriptan, rizatriptan, zolmitriptan, levodopa, tramadol, morphine and codeine.

Specific examples of food active ingredients preferably used in the present invention are calcium, phosphorus, magnesium, zinc, iron, serine, glutamine, arginine, vitamin C, vitamin A, vitamins of the B group, pantothenic acid, folic acid, vitamin D, vitamin K, niacin, proline, glucosamine, chondroitin sulphate, resveratrol, polycosanols, such as octacosanol, lipoic acid, melatonin, extracts of harpagofito, boswellia, echinacea, gingko biloba, garlic, hypericum and bilberry.

The quantity of active ingredient used in preparing the pharmaceutical or food formulation according to the present invention is preferably between 3% by weight and 60% by weight relative to the total weight of the pharmaceutical form, more preferably between 10% and 50% by weight, and even more preferably between 20% and 50% by weight.

The pharmaceutical or food form according to the present invention may be represented by any composition which is useful for the controlled oral administration of a pharmaceutical or food active ingredient such as for example tablets, granules, pellets, capsules, lozenges and pills.

The pharmaceutical or food form according to the present invention may also comprise other pharmaceutically acceptable excipients together with the controlled release excipient according to the present invention.

The term pharmaceutically acceptable excipient is understood to comprise without any particular limitations any material which is suitable for the preparation of a pharmaceutical composition which is to be administered to a living being. As already discussed, depending upon the role performed, excipients are classified into (i) filler excipients, (ii) production excipients, (iii) preservative excipients, and (iv) presentation excipients. These materials, which are known in the art, are for example (i) diluents, absorbents, adsorbents, fillers and humectants, (ii) lubricants, binders, glidants, plasticisers and viscosity modifiers, (iii) preservatives, antimicrobials, antioxidants and chelating agents, and (iv) flavourings, sweeteners and colouring agents.

Preferably the pharmaceutical or food form according to the present invention is a tablet comprising (i) at least one active ingredient, (ii) a controlled release system comprising a mixture of a glycogen with a polysaccharide, and (iii) at least one production excipient selected from the group comprising a glidant and a lubricant.

The glidant is added to improve the powder and render it homogeneous and its flow constant during the step of preparing the pharmaceutical or food form. The lubricant is added to encourage expulsion of the pharmaceutical or food form from the mould used to produce it, such as for example, from the punches used to compress the ingredients.

Advantageously, the glidant is selected from the group comprising colloidal silica, magnesium silicate, magnesium trisilicate and talc. The preferred glidant is colloidal silica.

Advantageously, the lubricant selected from the group comprising fatty acids and their salts such as for example stearic acid, magnesium stearate, calcium stearate, calcium palmitate and sodium stearyl fumarate, long-chain alcohols such as for example stearyl alcohol, stearic alcohol and cetyl alcohol, and glycerides such as for example glyceryl-behenate. The preferred lubricant is magnesium stearate or sodium stearyl fumarate.

The present invention also includes the procedure for producing the pharmaceutical or food form comprising at least one active ingredient dispersed in a mixture of a glycogen with a polysaccharide as described previously.

The present invention therefore comprises a process for the production of a pharmaceutical or food form comprising at least one active ingredient dispersed in a mixture of a glycogen with a polysaccharide, which comprises the steps of:
   mixing said glycogen and said polysaccharide with said active ingredient, and
   manufacturing the desired pharmaceutical or food form.

Advantageously the pharmaceutical or food form is selected from the group comprising tablets, granules, pellets, capsules, lozenges and pills.

Preferably said process for the production of a pharmaceutical or food form comprises the steps of:
   (i) mixing said glycogen and said polysaccharide with said active ingredient,
   (ii) granulating the composition obtained in step (i),
   (iii) mixing the granulate obtained in step (ii) with a glidant agent,
   (iv) mixing the composition obtained in step (iii) with a lubricating agent, and
   (v) manufacturing the desired pharmaceutical or food form.

Step (i) of mixing the glycogen and said polysaccharide with said active ingredient is preferably carried out in a fluidised bed granulator. Subsequently granulation step (ii) is preferably carried out in the same fluidised bed granulator with demineralised water. The granulate is then dried and then sieved preferably through 18 mesh.

Mixing steps (iii) and (iv) are preferably carried out in a single mixer until homogeneous dispersion is obtained, in order to ensure a constant and uniform flow of the resulting composition.

Production of the final pharmaceutical form in step (v) is performed using conventional techniques, preferably used in order to obtain tablets, granulates, pellets, capsules, lozenges and pills, which can comprise the steps of granulation, drying, mixing, grinding, sieving, compression, and so on.

Advantageously said process for the production of a pharmaceutical or food form comprises the steps of:
   (a) mixing said glycogen with a glidant agent,
   (b) mixing the composition in step (a) with said active ingredient and said polysaccharide,
   (c) mixing the composition in step (b) with a lubricating agent, and
   (d) manufacturing the desired pharmaceutical or food form.

Step (a) of mixing the glycogen with a glidant agent is preferably carried out in the first mixer until a homogeneous dispersion is obtained, so as to guarantee constant and uniform flow for the resulting composition.

Mixing step (b) is preferably carried out by first mixing the active ingredient with the polysaccharide in the second mixer and then adding and mixing the composition in step (a) discharged from the first mixer in order to obtain a homogeneous dispersion.

Mixing step (c) is preferably carried out by adding and mixing the lubricating agent in said second mixer.

Manufacture of the final pharmaceutical form in step (d) is performed using conventional techniques, preferably used for obtaining tablets, granules, pellets, capsules, lozenges and pills, which may comprise the steps of granulation, drying, mixing, grinding, sieving, compression, and so on.

The following examples will illustrate the invention without however restricting it.

EXAMPLE 1

Preparation of Tablets 1-3 (Invention)

A series of tablets from 1 to 3 containing the ingredients in Table 1 were prepared using the following procedure. Excipient 2 and the glidant were mixed for approximately 2 minutes and passed through an 18 mesh sieve. Excipient 1 was first loaded into a mixer, followed by the active ingredient and finally the mixture of excipient 2 and glidant. The composition was mixed for approximately 10 minutes. Mixing was then interrupted, and the lubricant was added. After mixing for a further approximately 3 minutes the composition was discharged from the mixer and compressed in a tabletting machine.

The quantity of active ingredient, excipient 1 and excipient 2 were weighted in such a way as to give a ratio by weight between them of 3:1:1 for tablet 1, 3:1:2 for tablet 2 and 3:1:3 for tablet 3.

TABLE 1

|  |  | 1 | 2 | 3 |
|---|---|---|---|---|
| Active ingredient | Paracetamol | 360 | 300 | 257 |
| Excipient 1 | Methocel K100M | 120 | 100 | 85.7 |
| Excipient 2 | Polglumyt | 120 | 200 | 257 |
| Glidant | Aerosil | 3 | 3 | 3 |
| Lubricant | PRUV | 9 | 9 | 9 |

Polglumyt ®: Glycogen comprising less than 60 ppm of nitrogen and less than 0.25% by weight of reducing sugars prepared according to the procedure described in EP 654.048.
MethocelV K100M: High viscosity hydroxypropylmethylcellulose (100,000 mPa · s) produced by Dow Chemical Co., USA
Aerosil ®: colloidal silica produced by Degussa AG, Germany
PRUV ®: sodium stearyl fumarate, produced by JRS Pharma GmbH, Germany Tablets 1-3 were subjected to a dissolution test in a paddle agitator (USP Apparatus 2) under the following conditions:
Rotation speed: 100 rpm
Medium: Potassium hydrogen phosphate buffer at pH 6.0
Container volume: 1000 ml
Temperature: 37° C.
UV analysis: 286 nm
Analysis time: up to 24 hours The results for the dissolution test for tablets 1-3 are shown in FIG. 1.

EXAMPLE 2

Preparation of Tablets 4-6 (Comparison)

A series of tablets from 4 to 6 containing the ingredients in Table 2 were prepared according to the same procedure as in Example 1.

TABLE 2

|  |  | 4 | 5 | 6 |
|---|---|---|---|---|
| Active ingredient | Paracetamol | 360 | 300 | 257 |
| Excipient 1 | Methocel K100M | 120 | 100 | 85.7 |
| Excipient 2 | Avicel PH200 | 120 | 200 | 257 |
| Glidant | Aerosil | 3 | 3 | 3 |
| Lubricant | PRUV | 9 | 9 | 9 |

Figure 2:
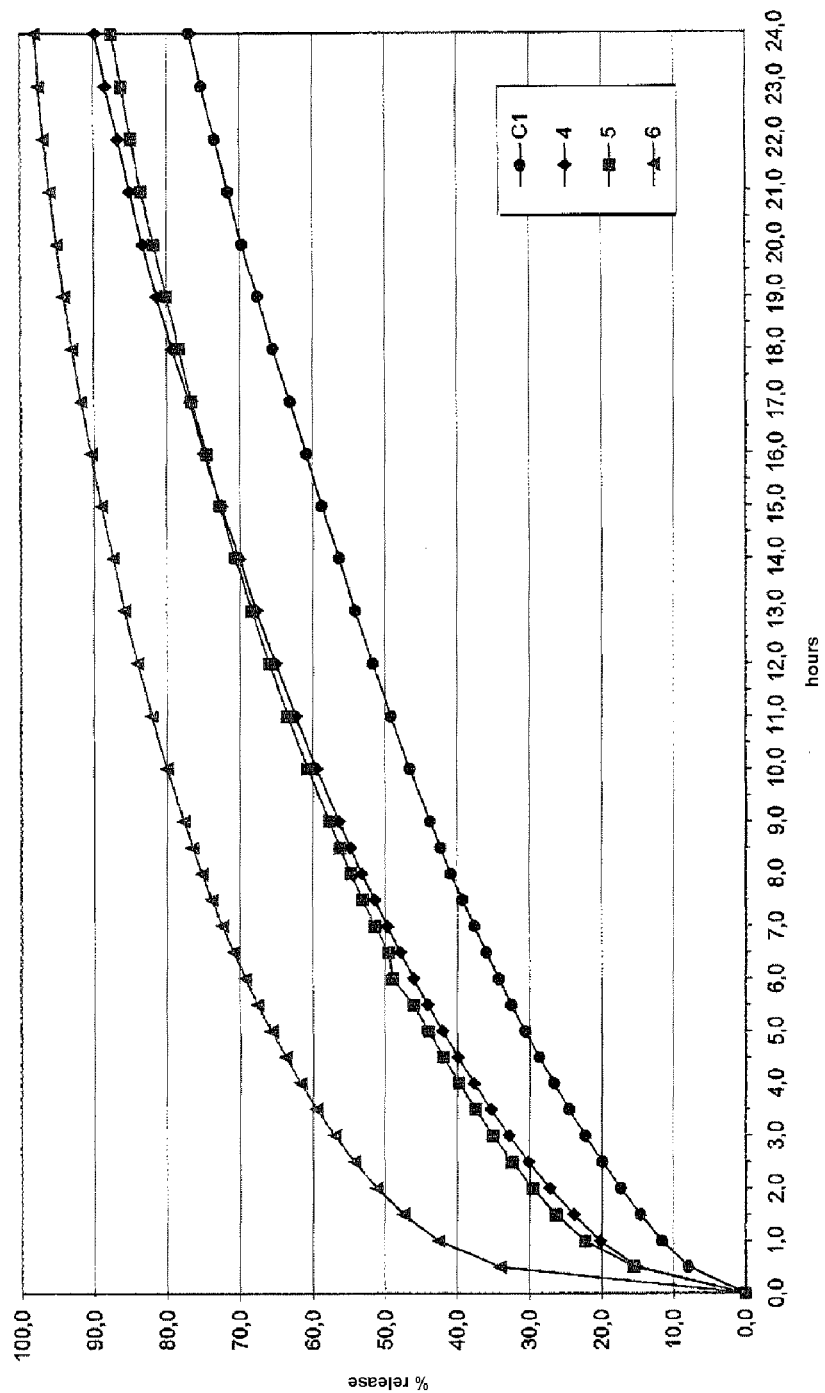
FIG. 2 illustrates the release profile for tablets 4, 5 and 6 in Example 2 compared with that for tablet C1.

Avicel ®PH200: Microcrystalline cellulose having nominal dimensions of 180 μm, produced by FMC BioPolymer, USA Tablets 4-6 were subjected to the same dissolution test as in Example 1 under the same conditions. The results of the dissolution test for tablets 4-6 are shown in FIG. 2.

EXAMPLE 3

Preparation of Tablets 7-9 (Comparison)

A series of tablets from 7 to 9 containing the ingredients in Table 3 were prepared according to the same procedure as in Example 1.

TABLE 3

|  |  | 7 | 8 | 9 |
|---|---|---|---|---|
| Active ingredient | Paracetamol | 360 | 300 | 257 |
| Excipient 1 | Methocel K100M | 120 | 100 | 85.7 |
| Excipient 2 | Lactose | 120 | 200 | 257 |
| Glidant | Aerosil | 3 | 3 | 3 |
| Lubricant | PRUV | 9 | 9 | 9 |

Figure 3:
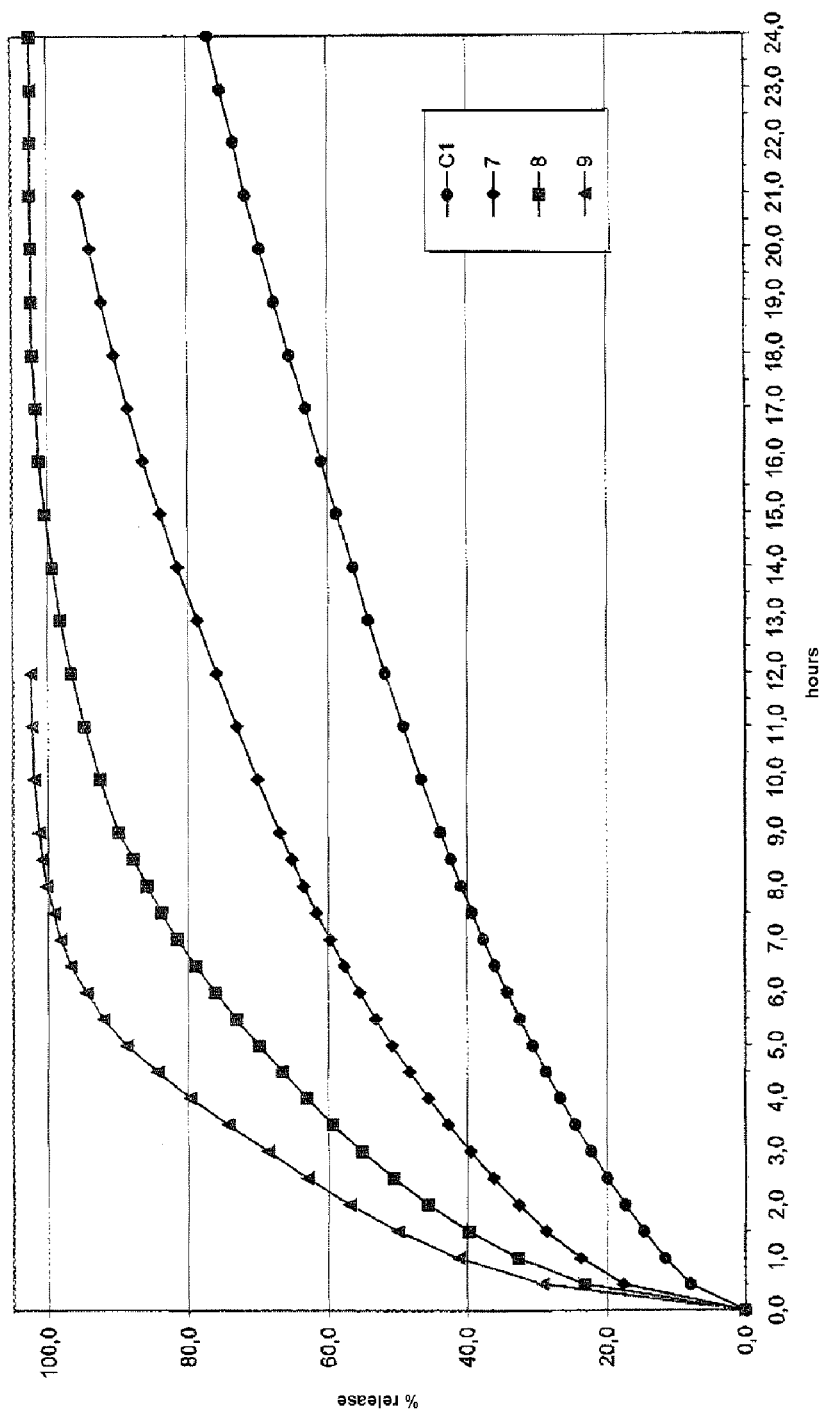
FIG. 3 illustrates the release profile for tablets 7, 8 and 9 in Example 3 compared with that for tablet C1.

Tablets 7-9 were subjected to the same dissolution test as in Example 1 under the same conditions. The results of the dissolution test for tablets 7-9 are shown in FIG. 3.

EXAMPLE 4

Preparation of Tablets 10-11 (Comparison)

A series of tablets from 10 to 11 containing the ingredients in Table 4 were prepared according to the same procedure as in Example 1.

TABLE 4

|  |  | 10 | 11 |
|---|---|---|---|
| Active ingredient | Paracetamol | 360 | 257 |
| Excipient 1 | Methocel K100M | 120 | 85.7 |
| Excipient 2 | $CaHPO_4$ | 120 | 257 |
| Glidant | Aerosil | 3 | 3 |
| Lubricant | PRUV | 9 | 9 |

Figure 4:
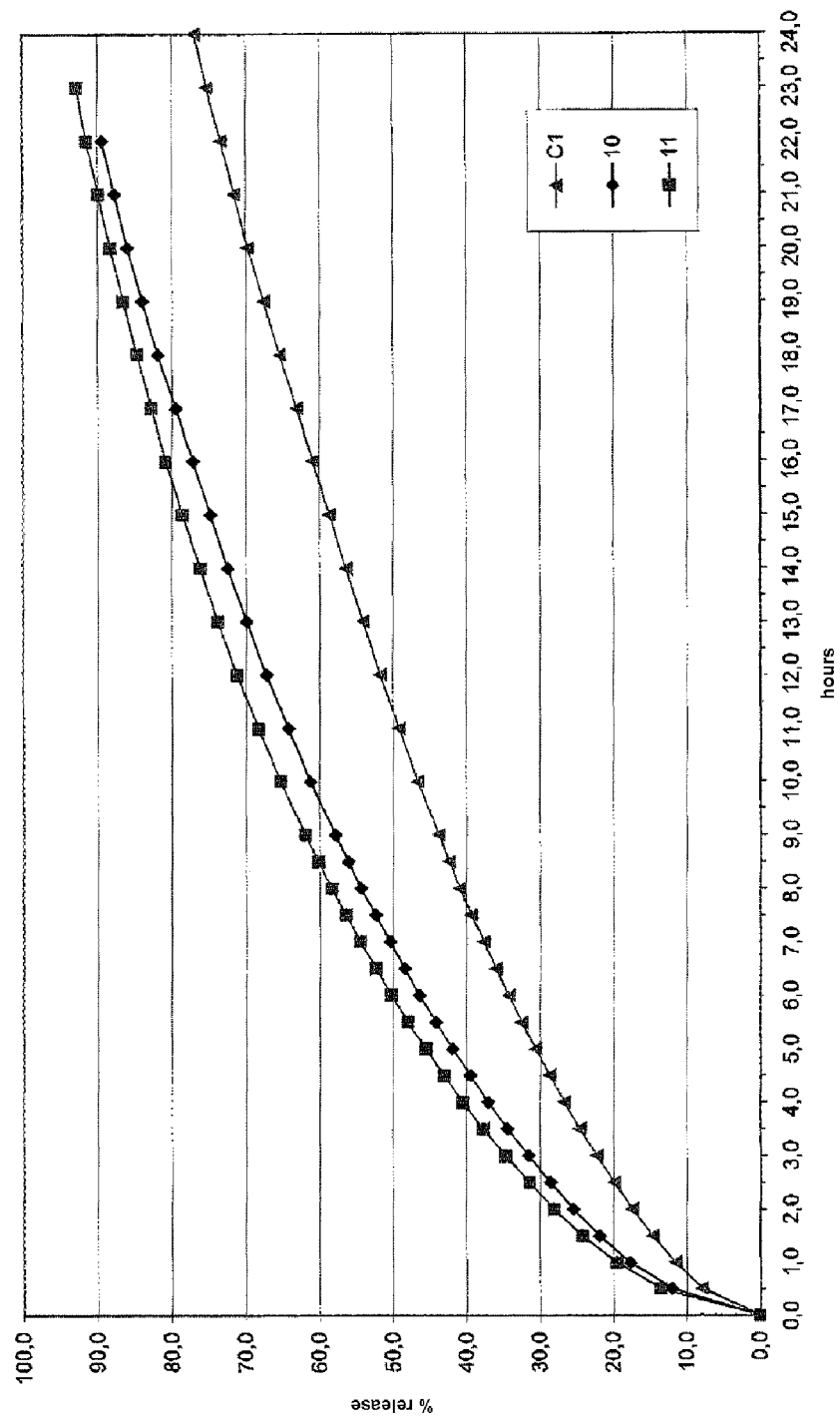
FIG. 4 illustrates the release profile for tablets 10 and 11 in Example 4 compared with that for tablet C1.

Tablets 10-11 were subjected to the same dissolution test as in Example 1 under the same conditions. The results of the dissolution test for tablets 10-11 are shown in FIG. 4.

The quantities of components shown in Tables 1 to 4 are expressed in milligrams.

All the Figures from 1 to 4 also show the progress of dissolution (under the same conditions as in Example 1) of a comparison tablet C1 comprising 450 mg of active ingredient (Paracetamol), 150 mg of excipient 1 (Methocel K100M), 3 mg of glidant (Aerosil) and 9 mg of lubricant (PRUV). Tablet C1 was prepared by loading excipient 1 first into a mixer, followed by the active ingredient and finally the glidant. The composition was mixed for approximately 10 minutes. Mixing was then interrupted, and the lubricant was added. After mixing for a further approximately 3 minutes the composition was discharged from the mixer and compressed in the tabletting machine. The quantity of active ingredient and excipient 1 in tablet C1 was weighted in such a way as to give a ratio by weight between them of 3:1.

From a comparison of the graphs shown in FIGS. 1 to 4 it is clear that the combination of excipient 1 (Methocel K100M) with another excipient modifies the release kinetics shown by tablet C1 containing excipient 1 alone.

The comparison combinations (tablets 4-11) have clearly demonstrated an increase in the initial release of active ingredient and worsening of the deviation from linearity, with a release curve characterized by first order kinetics, dependent on the quantity of active ingredient present in the tablets.

Conversely, the combinations according to the invention (tablets 1-3) have clearly demonstrated that in addition to increased total release of active ingredient, amounting to almost 100% over a 24-hour period, there is also a decrease in deviation from linearity, with a release curve characterized by substantially zero order kinetics, independent from the quantity of active ingredient present in the tablet.

Subsequent Table 5 shows the linear correlation coefficients for tablets C1 and 1-11 calculated at the indicated dissolution time.

TABLE 5

| Tablet | linear correlation coefficient at: | | |
|---|---|---|---|
| | 4 hours | 6 hours | 10 hours |
| C1 | 0.886 | 0.878 | 0.864 |
| 1 | 0.962 | 0.954 | 0.935 |
| 2 | 0.990 | 0.990 | 0.981 |
| 3 | 0.999 | 0.999 | 0.988 |
| 4 | 0.713 | 0.685 | 0.666 |
| 5 | 0.687 | 0.648 | 0.589 |
| 6 | 0.319 | 0.100 | 0.398 |
| 7 | 0.740 | 0.706 | 0.653 |
| 8 | 0.755 | 0.700 | 0.597 |
| 9 | 0.757 | 0.702 | 0.388 |
| 10 | 0.828 | 0.808 | 0.785 |
| 11 | 0.816 | 0.788 | 0.752 |

The data in Table 5 have confirmed that the combination according to the present invention (tablets 1-3) is the only one capable of improving the linear correlation, which approaches a value of 1, while all the comparison combinations produce worsening of the linear correlation in comparison with the reference represented by tablet C1.

Comparison between the three tablets according to the present invention shows that the best linear correlation was obtained with tablet 3 comprising a weight ratio of active ingredient to excipient 1 and excipient 2 of 3:1:3.

EXAMPLE 5

Preparation of Tablets 12-15

A series of tablets from 12 to 15 containing the ingredients in Table 6 were prepared using the same procedure as in Example 1. Tablet C2 was prepared using the same procedure as for tablet C1. Quantities are expressed in milligrams.

TABLE 6

| | | C2 | 12 | 13 | 14 | 15 |
|---|---|---|---|---|---|---|
| Active ingredient | Paracetamol | 450 | 360 | 300 | 257 | 257 |
| Excipient 1 | Methocel K100LV | 150 | 120 | 100 | 85.7 | 43 |
| Excipient 3 | Methocel K100M | — | — | — | — | 43 |
| Excipient 2 | Polglumyt | — | 120 | 200 | 257 | 257 |
| Glidant | Aerosil | 3 | 3 | 3 | 3 | 3 |
| Lubricant | PRUV | 9 | 9 | 9 | 9 | 9 |

Figure 5:
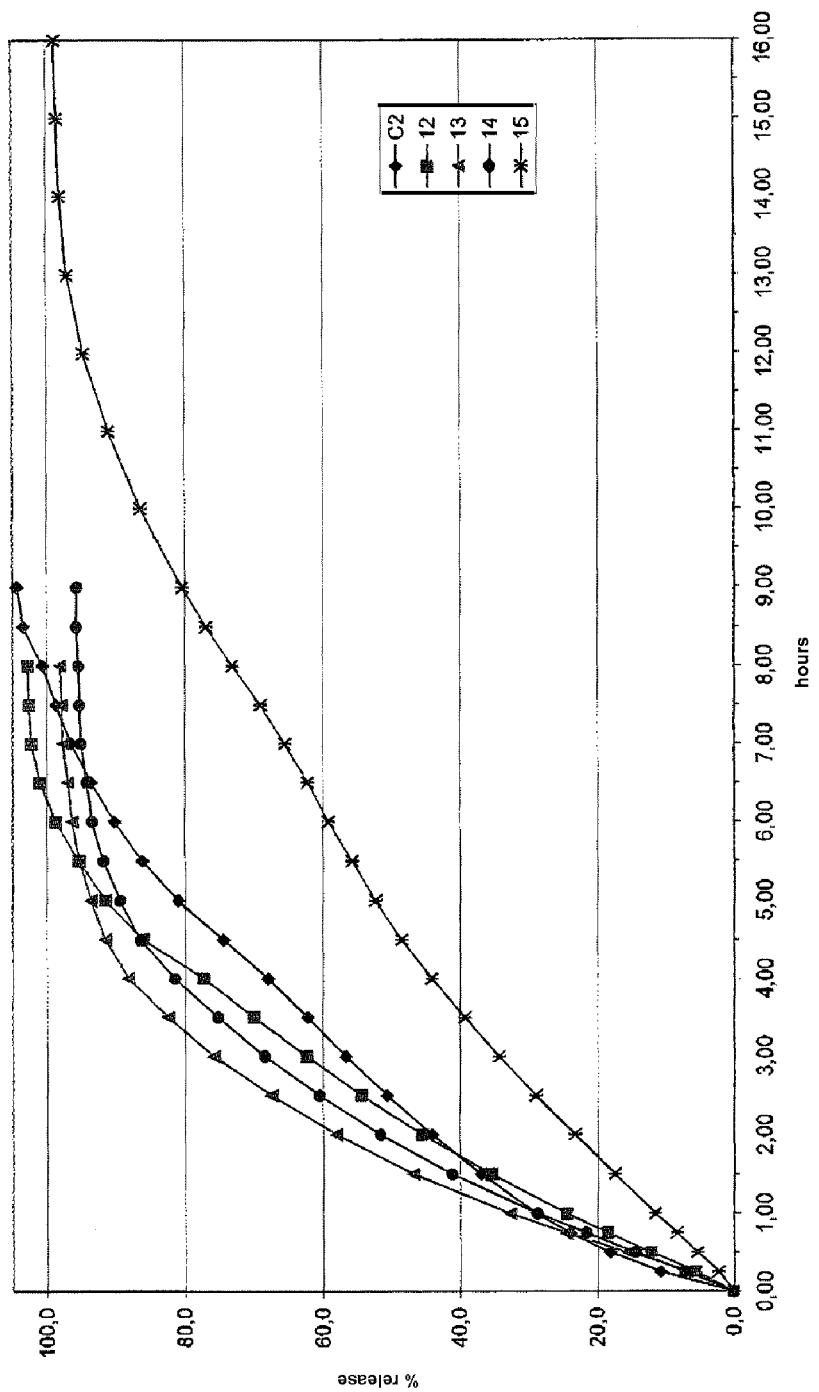
FIG. 5 illustrates the release profile for tablets 12 to 15 in Example 5 compared with that for tablet C2.

Methocel K100 LV: Low viscosity hydroxypropylmethylcellulose (100 mPa·s) produced by Dow Chemical Co., USA Tablets 12-15 were subjected to a dissolution test in a paddle agitator (USP Apparatus 2) under the following conditions:
Rotation speed: 100 rpm
Medium: Potassium hydrogen phosphate buffer at pH 6.0
Container volume: 1000 ml
Temperature: 37° C.
UV analysis: 286 nm
Analysis time: up to 24 hours
The results of the dissolution test for tablets 12-15 and tablet C2 are shown in FIG. 5.

EXAMPLE 6

Preparation of Tablets 16 and C3

Tablet 16 containing the ingredients in Table 7 was prepared according to the procedure for Example 1. Tablet C3 containing the ingredients in Table 7 was prepared according to the procedure described for tablet C1.

The quantities of active ingredient, excipient 1 and excipient 2 in tablet 16 were weighted in such a way as to provide a ratio by weight between them of 3:1:3. The quantities of active ingredient and excipient 1 in tablet C3 were weighted in such a way as to give a ratio by weight between them of 3:1. Quantities are expressed in milligrams.

TABLE 7

| | | 16 | C3 |
|---|---|---|---|
| Active ingredient | Paracetamol | 257 | 450 |
| Excipient 1 | Xantural 75 | 85.7 | 150 |
| Excipient 2 | Polglumyt | 257 | — |
| Glidant Flow enhancer | Aerosil | 3 | 3 |
| Lubricant | PRUV | 9 | 9 |

Figure 6:
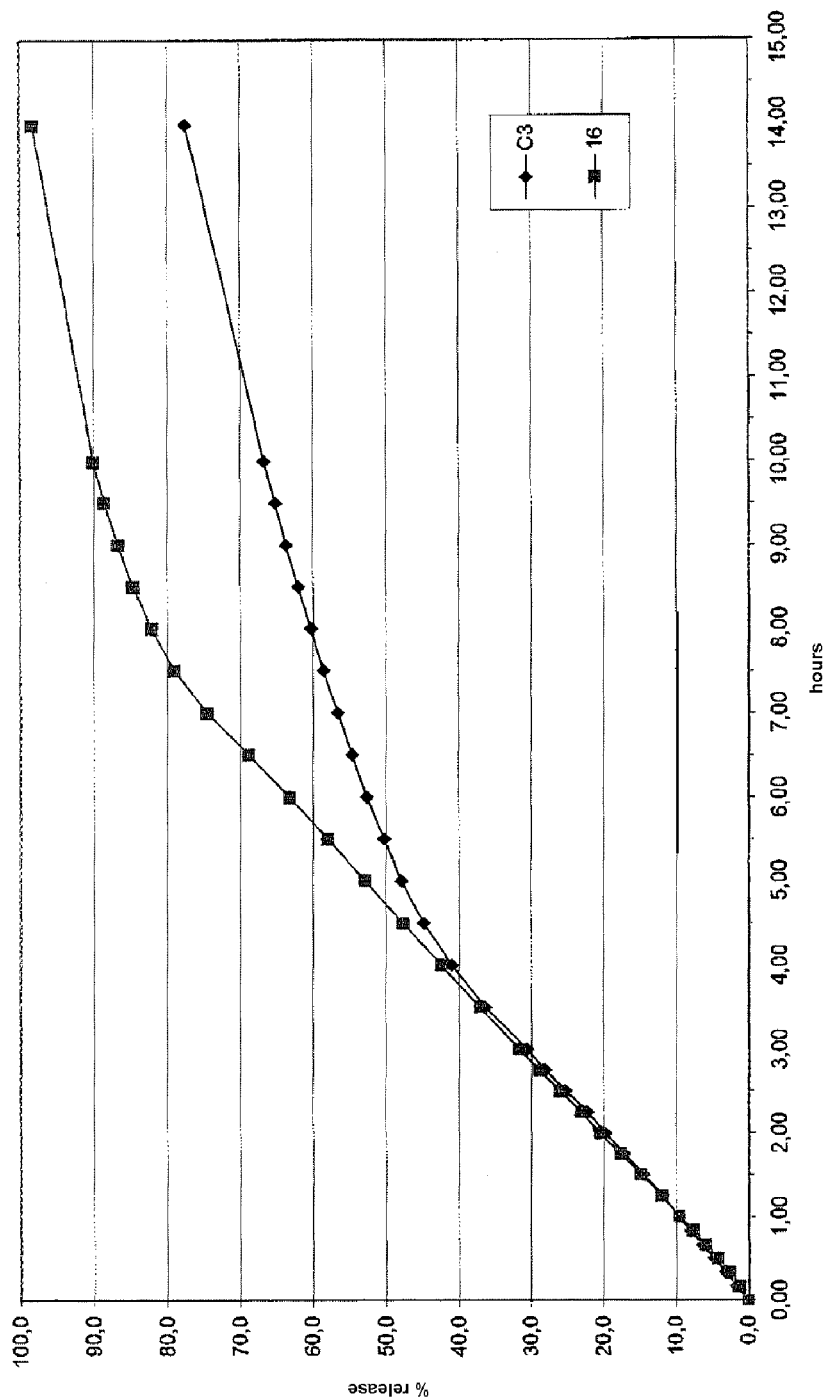
FIG. 6 illustrates the release profile for tablet 16 in Example 6 compared with that for tablet C3.

Xantural ® 75: Fine grain xanthan gum (75 µm) produced by CP Kelco, Atlanta, GA, USA Tablets 16 and C3 were subjected to a dissolution test in a BioDis agitator (USP Apparatus 3) under the following conditions:
Dipping rate: 100 dpm
Medium: Potassium hydrogen phosphate buffer at pH 6.0
Container volume: 250 ml
Temperature: 37° C.
UV analysis: 286 nm
Analysis time: up to 14 hours
The results of the dissolution test for tablets 16 and C3 are shown in FIG. 6.

The graph in FIG. 6 clearly shows that again in this case the tablet containing the combination of excipient 1 (Xantural 75) and excipient 2 (Polglumyt) reveals better release kinetics than the tablet containing excipient 1 alone.

In particular, comparison tablet C3 shows a sudden change in release kinetics at approximately 240 minutes and a maximum release of active ingredient which reaches 80% w/w at approximately 15 hours. Tablet 16 according to the invention instead showed an increase in percentage total release which amounted to almost 100% at approximately 15 hours, and a significant prolongation of linearity. Subsequent Table 8 shows the linear correlation coefficients for tablets C3 and 16 calculated at the dissolution time indicated.

TABLE 8

| Tablet | linear correlation coefficient at: | | | |
|---|---|---|---|---|
| | 240 min | 330 min | 450 min | 600 min |
| C3 | 0.998 | 0.994 | 0.971 | 0.936 |
| 16 | 0.998 | 0.998 | 0.999 | 0.990 |

The data in Table 8 confirm that the combination according to the present invention improves the linear correlation, approaching the theoretical value of 1, even when a hydrophilic polymer like xanthan gum is used as excipient 1.

EXAMPLE 7

Comparison tablets C1 and C3 and the tablets according to the invention 3 and 17 were subjected to compression and extraction tests to evaluate whether their technological characteristics were suitable for production on an industrial scale.

In particular, the tablets were subjected to an evaluation of hardness using an Erweka series TBH hardness meter, the compression force required in the tabletting machine in order to prepare them, and the extraction force necessary to remove them from their dies. The tablets were also checked to verify whether or not detachment of portions of the tablet ("capping") and sticking occurred.

The results are summarized in Table 9 below.

TABLE 9

|  | C1 | 3 | C3 | 17 |
|---|---|---|---|---|
| Mean hardness (Kp) | 6.34 | 10.61 | 1.20 | 10.72 |
| Compression force (kN) | 38-40 | 28 | 38 | 30 |
| Extraction force (N) | 250 | 250 | <250 | <250 |
| Capping | No | No | Partial | No |
| Sticking | No | No | No | No |

The data in Table 9 showed that the hardness of tablets C1 and C3 was too low to withstand the stresses to which they would be subjected during industrial production, and the compression force was too high. Table C3 also showed partial capping. Industrial production of tablets C1 and C3 would not be possible as such, but would require the presence of further excipients which might further modify the release profile. Conversely, tablets 3 and 17 comprising the combination according to the present invention showed optimum hardness obtained with a compression force of approximately 28-30 kN. It was not therefore necessary to add further excipients, and the tablets proved to be perfectly capable of being produced on an industrial scale.

EXAMPLE 8

Preparation of Tablets 17 and 18

Tablets 17 and 18 containing the ingredients in Table 10 were prepared using the same procedure as for Example 1. Quantities are expressed in milligrams.

TABLE 10

|  |  | 17 | 18 |
|---|---|---|---|
| Active ingredient | Trazodone hydrochloride | 300 | — |
|  | Paracetamol | — | 300 |
| Excipient 1 | Methocel K100M | 100 | 100 |
| Excipient 2 | Polglumyt | 200 | 200 |
| Glidant Flow enhancer | Aerosil | 3 | 3 |
| Lubricant | PRUV | 9 | 9 |

Paracetamol is an active ingredient whose solubility is independent of the pH of the dispersing medium. Trazodone hydrochloride is an active ingredient having a solubility which depends on the pH of the dispersing medium.

Tablets 17 and 18 were subjected to a dissolution test in a paddle agitator (USP Apparatus 2) under the following conditions:

Rotation speed: 100 rpm
Container volume: 1000 ml
Temperature: 37° C.
UV analysis: 286 nm (paracetamol)
247 nm (trazodone hydrochloride)
Analysis time: up to 24 hours The medium used was a solution of 0.1 N HCl (pH 1.2) during the first hour, which was then corrected to pH=6.0 using potassium hydrogen phosphate buffer solution during the subsequent hours to the end of the test (medium 1). A test was also performed using tablet 18 in a potassium hydrogen phosphate buffer solution at pH=6.0 for the entire period of the test (medium 2).

Figure 7:
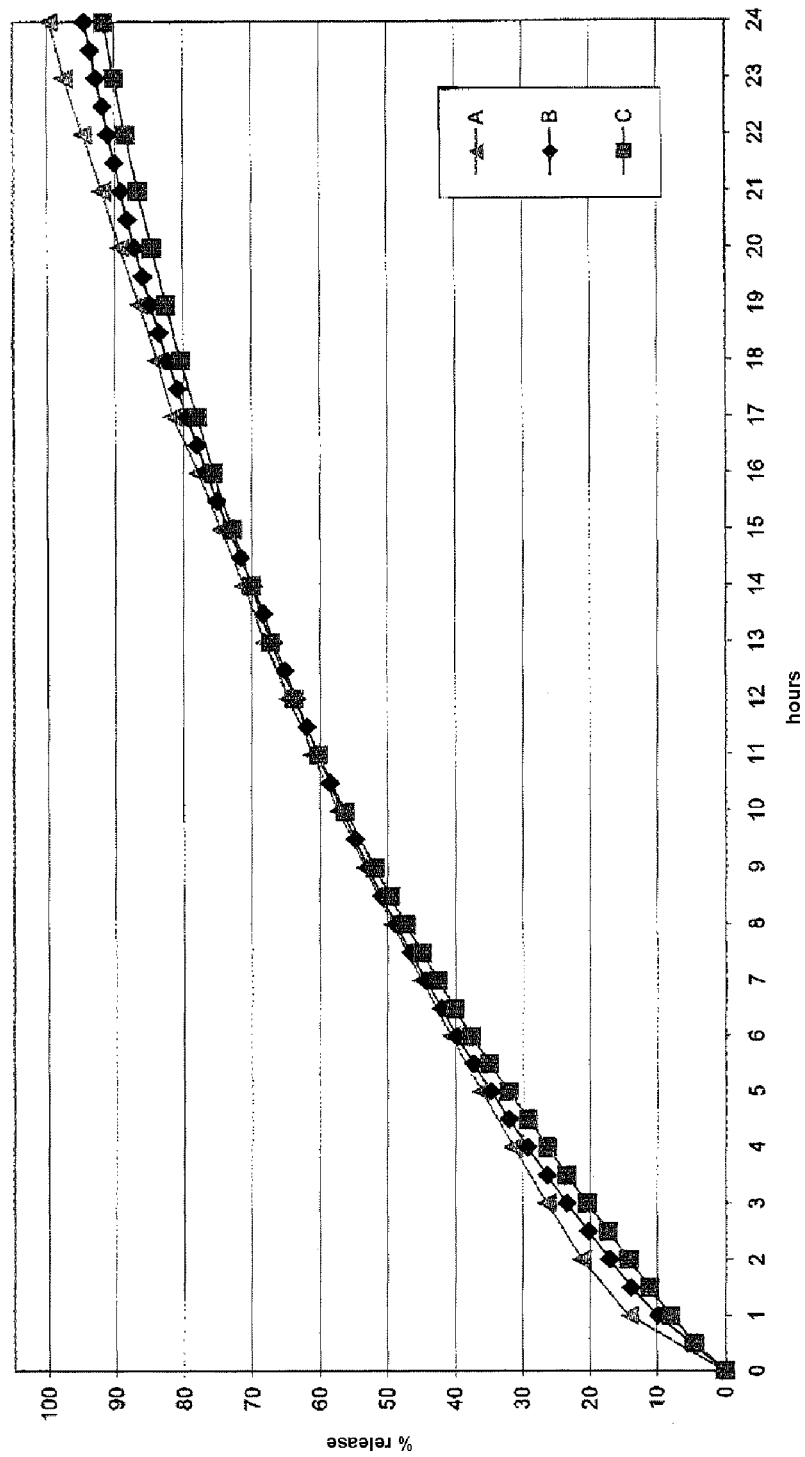
FIG. 7 illustrates the release profile for tablets 17 and 18 in Example 8.

The results of the dissolution test for tablets 17 and 18 are shown in FIG. 7.

Release profile A corresponds to the release of tablet 17 in medium 1, release profile B corresponds to release of tablet 18 in medium 1, and release profile C corresponds to release of tablet 18 in medium 2. The three profiles substantially confirmed the linearity, time and release quantity characteristics in the preceding examples.

Furthermore, notwithstanding the substantial chemical and physical difference between the active ingredients, under the same conditions of the dispersing medium and pH, the release profiles for tablets 17 and 18 (graphs A and B) are substantially identical. The combination according to the present invention can therefore be used for active ingredients having solubility characteristics which are even quite different from each other.

Finally, for the same active ingredient (paracetamol), the release profiles for tablet 18 (graphs B and C) in the two dispersing media of different pH proved to be substantially identical. The combination according to the present invention therefore made it possible to achieve a release profile which was substantially independent of the pH of the dispersing medium.

EXAMPLE 9

Preparation of Tablet 19

Tablet 19 containing the ingredients in Table 11 was prepared according to the following procedure. Excipient 1, excipient 2 and the active ingredient were mixed for approximately 3 minutes in a fluidized bed granulator and subsequently granulated with demineralized water. After drying and sieving through 18 mesh the above composition was loaded into a mixer and glidant was added to it. The composition was mixed for approximately 10 minutes. Mixing was then interrupted, and the lubricant was added. After mixing for a further approximately 3 minutes the composition was discharged from the mixer and compressed in a tabletting machine.

The quantities of active ingredient, excipient 1 and excipient 2 were weighted in such a way as to yield a ratio by weight between them of 3:1:3.

TABLE 11

|  |  | 19 |
|---|---|---|
| Active ingredient | Paracetamol | 257 |
| Excipient 1 | Methocel K100M | 85.7 |
| Excipient 2 | Polglumyt | 257 |
| Glidant | Aerosil | 3 |
| Lubricant | PRUV | 9 |

EXAMPLE 10

Preparation of Tablets 20-21

A series of tablets from 20 to 21 containing the ingredients in Table 12 were prepared according to the following procedure. Excipient 2 and the glidant were mixed for approximately 2 minutes and passed through an 18 mesh sieve. Excipient 1 was first loaded into a mixer, followed by the active ingredient(s) and finally the mixture of excipient 2 and glidant. The composition was mixed for approximately 10 minutes. Mixing was then interrupted, and the lubricant was added. After mixing for a further approximately 3 minutes the composition was discharged from the mixer and compressed in a tabletting machine.

TABLE 12

|  |  | 20 | 21 |
|---|---|---|---|
| Functional principle | Harpagofito root | 110 | — |
| Functional principle | Harpagofito, dried extract (*) | 60 | — |
| Functional principle | Vitamin C | — | 240 |
| Excipient 1 | Methocel K100M | 100 | 100 |
| Excipient 2 | Polglumyt | 200 | 200 |
| Glidant | Aerosil | 3 | 3 |
| Lubricant | PRUV | 9 | 9 |

(*) titrated at 2.5% glycoiridoid

The invention claimed is:

1. A controlled release pharmaceutical or food formulation, consisting of
    at least one active ingredient dispersed in a mixture of glycogen with a polysaccharide other than alginate wherein said at least one active ingredient is released in the gastrointestinal tract over at least 1 hour and the release kinetics of said at least one active ingredient are substantially of zero order
    wherein a ratio by weight between the glycogen and the polysaccharide is between 10:1 and 1:5, and
    said formulation, optionally, contains at least one pharmaceutically acceptable excipient.

2. The formulation of claim 1, wherein said pharmaceutically acceptable excipient is selected from the group consisting of a filler excipient, a production excipient, a preservative excipient, and a presentation excipient.

3. The formulation of claim 1, wherein said pharmaceutically acceptable excipient is selected from the group consisting of a diluent, an absorbent, an adsorbent, a filler, a humectant, a lubricant, a binder, a glidant, a plasticizer, a viscosity modifier, a preservative, an antimicrobial, an antioxidant, a chelating agent, a flavouring, a sweetener, and a colouring agent.

4. The formulation of claim 1, wherein the glycogen comprises less than 1% by weight of reducing sugars.

5. The formulation of claim 4, wherein the glycogen comprises less than 0.25% by weight of reducing sugars.

6. The formulation of claim 1, wherein the glycogen comprises less than 3000 ppm of nitrogen.

7. The formulation of claim 6, wherein the glycogen comprises less than 1000 ppm of nitrogen.

8. The formulation of claim 6, wherein the glycogen comprises less than 100 ppm of nitrogen.

9. The formulation of claim 1, wherein the polysaccharide is at least one selected from the group consisting of a cellulose, a gum, a carrageenan, a mannane, and a further hydrophilic polysaccharide.

10. The formulation of claim 9, wherein cellulose is present and is at least one selected from the group consisting of microcrystalline cellulose, an alkylcellulose, a hydroxyalkylcellulose, a hydroxyalkymethylcellulose, a hydroxyalkylalkylcellulose, and a carboxyalkylcellulose.

11. The formulation of claim 9, wherein the gum is present and is at least one selected from the group consisting of xanthan gum, gum arabic, gum tragacanth, gellan gum, and ghatti gum.

12. The formulation of claim 9, wherein the carrageenan is present and is at least one selected from the group consisting of Kappa-carrageenan, Lambda-carrageenan, and Iota-carrageenan.

13. The formulation of claim 9, wherein the mannane is present and is at least one selected from the group consisting of carob gum, tara gum, and guar gum.

14. The formulation of claim 9, wherein the other hydrophilic polysaccharide is present and is at least one selected from the group consisting of agar, pectin, inulin, chitosan, and chitin.

15. The formulation of claim 9, wherein the polysaccharide is at least one selected from the group consisting of a cellulose.

16. The formulation of claim 15, wherein the polysaccharide has a viscosity of between 100 and 100,000 mPa·s, with reference to a 2% w/v aqueous solution at 20° C.

17. The formulation of claim 1, wherein a ratio by weight between the glycogen and the polysaccharide is between 5:1 and 1:2.

18. The formulation of claim 1, wherein a quantity of the active ingredient is between 3% by weight and 60% by weight relative to a total weight of the pharmaceutical formulation.

19. The formulation of claim 1, wherein the active ingredient is at least one pharmaceutical active ingredient selected from the group consisting of an analgesic, an antipyretic, an antibiotic, an antihistamine, an anxiolytic, an anti-inflammatory, an antacid, a vasodilator, a vasoconstrictor, a stimulant, a decongestant, an anticoagulant, an antiarrhythmic, a hypoglycaemizing agent, a diuretic, an antidepressant, an antiasthmatic, an antiemetic, an antihypertensive, a spasmolytic, an anti-tumour agent, a hormone, a muscle relaxant, an antiseptic, an antimycotic, an immunostimulant, an immunomodulant, an anti-migraine agent, an anti-Parkinson agent, a peptide, a drug of biological origin, and a biosimilar drug.

20. The formulation of claim 19, wherein the active ingredient is at least one selected from the group consisting of ibuprofen, paracetamol, prulifloxacin, levocetirizine dihydrochloride, lorazepam, naproxen, ranitidine hydrochloride, isosorbide, nafazoline nitrate, piracetam, ticlopidine hydrochloride, propafenone hydrochloride, glimepiride, furosemide, verapamil, trazodone hydrochloride, flunisolide, dimenhydrinate, diclofenac, a salt of diclofenac, ciprofloxacin, omeprazole, flurbiprofen, bindarit, sumatriptan, rizatriptan, zolmitriptan, levodopa, tramadol, morphine, and codeine.

21. The formulation of claim 1, wherein the active ingredient is at least one food active ingredient selected from the group consisting of a vitamin, a mineral, a plant extract, a mixture of straight and branched amino acid, and a biotechnology product.

22. The formulation of claim 21, wherein the active ingredient is at least one food active ingredient selected from the group consisting of calcium, phosphorus, magnesium, zinc, iron, serine, glutamine, arginine, vitamin C, vitamin A, a vitamin of the B group, pantothenic acid, folic acid, vitamin D, vitamin K, niacin, proline, glucosamine, chondroitin sulphate, resveratrol, a polycosanol, lipoic acid, melatonin, an extract of harpagofito, boswellia, echinacea, gingko biloba, garlic, hypericum, and bilberry.

23. The formulation of claim 1, wherein said at least one active ingredient is released in the gastrointestinal tract over at least 3 hours.

24. The formulation of claim 1, wherein said at least one active ingredient is released in the gastrointestinal tract over at least 6 hours.

25. The formulation of claim 1, wherein said formulation is a controlled release pharmaceutical formulation.

26. The formulation of claim 1, wherein said formulation is a controlled release food formulation.

27. The formulation of claim 25, wherein the controlled release pharmaceutical formulation is in at least one form selected from the group a tablet, a granule, a pellet, a capsule, a lozenge, and a pill.

28. The formulation of claim 27, wherein said excipient is selected from the group consisting of a glidant and a lubricant.

29. The formulation of claim 28, wherein the glidant is present and is selected from the group consisting of colloidal silica, magnesium silicate, magnesium trisilicate, and talc.

30. The formulation of claim 28, wherein the lubricant is present and is at least one selected from the group consisting of a fatty acid, a salt of a fatty acid, a long-chain alcohol, and a glyceride.

31. A process for producing a pharmaceutical or food form consisting of at least one active ingredient dispersed in a mixture of glycogen with a polysaccharide other than alginate and, optionally, contains at least one pharmaceutically acceptable excipient, wherein said at least one active ingredient is released in the gastrointestinal tract over at least 1 hour, the process comprising:
  (a) mixing the glycogen and the polysaccharide with the active ingredient, wherein a ratio by weight between the glycogen and the polysaccharide is between 10:1 and 1:5; and
  (c) producing a desired pharmaceutical or food form wherein the release kinetics of said at least one active ingredient are substantially of zero order, and wherein said method further comprises optionally mixing at least one pharmaceutically acceptable excipient.

32. The process of claim 31, wherein the producing comprises:
  (ii) granulating the composition obtained in the mixing (a) and drying, to obtain a resultant granulate,
  (iii) mixing the resulting granulate obtained in (ii) with a glidant agent, to obtain a first intermediate composition,
  (iv) mixing the first intermediate composition obtained in (iii) with a lubricating agent, to obtain a second intermediate composition; and
  (v) manufacturing the a pharmaceutical or food form from the second intermediate composition.

33. The process of claim 31, further comprising, prior to the mixing (a):
  (a.0) mixing the glycogen with a glidant agent, to obtain a glidant composition, and, after the mixing (a),
  (c) mixing the composition from step (a) with a lubricating agent, wherein, in the mixing (a), the glycogen comprises the glidant composition.

34. The process of claim 31, wherein the pharmaceutical form is produced and is at least one selected from the group consisting of a tablet, a granule, a pellet, a capsule, a lozenge, and a pill.

* * * * *

UNITED STATES PATENT AND TRADEMARK OFFICE
CERTIFICATE OF CORRECTION

PATENT NO. : 9,125,823 B2  
APPLICATION NO. : 13/139192  
DATED : September 8, 2015  
INVENTOR(S) : Stefano Selva et al.

Page 1 of 1

It is certified that error appears in the above-identified patent and that said Letters Patent is hereby corrected as shown below:

Title page, item (75) Inventors: delete "Leonardo Marchitto, Porto Recanati (TW)" in its entirety and replace with the following:

--Leonardo Marchitto, Porto Recanati (IT)--

Signed and Sealed this  
Fifteenth Day of March, 2016

Michelle K. Lee  
*Director of the United States Patent and Trademark Office*